Figure 1:
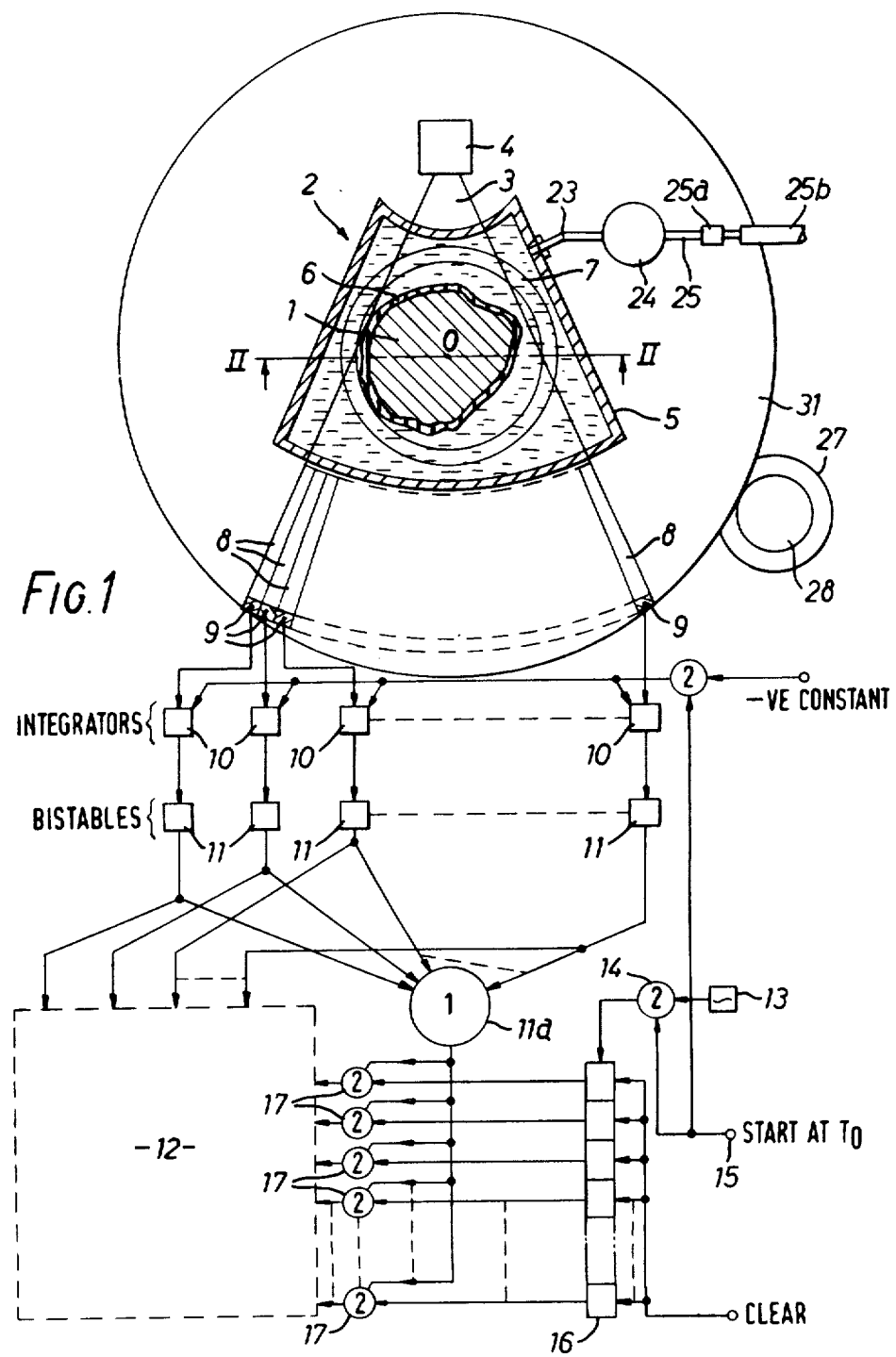

United States Patent

Hounsfield et al.

[11] 4,035,647
[45] July 12, 1977

[54] RADIOGRAPHY

[75] Inventors: Godfrey Newbold Hounsfield, Newark; David John Gibbons, Uxbridge, both of England

[73] Assignee: E M I Limited, Hayes, England

[21] Appl. No.: 481,443

[22] Filed: June 20, 1974

Related U.S. Application Data

[62] Division of Ser. No. 358,980, May 10, 1973, Pat. No. 3,881,110.

[30] Foreign Application Priority Data

May 17, 1972 United Kingdom ............ 23064/72

[51] Int. Cl.² .......................................... G01T 1/20
[52] U.S. Cl. .................... 250/366; 250/369; 250/445 T
[58] Field of Search ............ 178/DIG. 5; 250/363, 250/366, 402, 369, 454, 445 T

[56] References Cited

U.S. PATENT DOCUMENTS

| 3,372,276 | 3/1968 | Reynolds et al. | 250/363 X |
| 3,432,657 | 3/1969 | Slavin | 250/360 |
| 3,766,387 | 10/1973 | Heffan et al. | 250/360 |
| 3,854,047 | 12/1974 | Suhami et al. | 250/366 |
| 3,944,833 | 3/1976 | Hounsfield | 250/367 |

Primary Examiner—Alfred E. Smith
Assistant Examiner—T. N. Grigsby
Attorney, Agent, or Firm—Fleit & Jacobson

[57] ABSTRACT

Apparatus is disclosed for producing a representation of the absorption coefficient, with respect to X- or γ-radiation, at a plurality of locations distributed over a planar section of a body under examination. The radiation is directed towards the body in a planar swath which embraces the section, and the radiation emergent from the body is detected by means of an array of detectors. The swath of radiation and the detector array are rotated steadily about an axis perpendicular to the plane of the swath, and passing through the body, so that the section is irradiated from a plurality of different directions.

8 Claims, 6 Drawing Figures

RADIOGRAPHY

This application is a divisional of Application Ser. No. 358,980 filed May 10, 1973 (now U.S. Pat. No. 3,881,110).

The present invention relates to radiography and it relates especially to techniques for obtaining information indicative of the presence or absence of anomalies in the interior of a body, despite the presence of other material in the body.

In the Specification of U.S. patent appliction Ser. No. 212,778 now U.S. Pat. No. 3,778,614 there is described and claimed a method of, and apparatus for, examining a body by means of radiation such as X- or γ-radiation. The use of the method or apparatus permits the calculation of the transmission or absorption coefficients of substantially all elements in an at least two dimensional, notional matrix of elements defined in the body being examined. This is achieved by causing radiation to pass through the body along a plurality of discrete paths of cross-sectional dimensions similar to those of said elements, said paths being oriented to pass through respective combinations of the elements in said notional matrix. The overall absorption of radiation along each of the discrete paths is detected and sufficient paths are used to enable the calculation of the absorption or transmission coefficients of substantially all elements in said notional matrix.

It is an object of this invention to provide apparatus for examining part of a body by means of penetrating radiation, such as X- or γ-radiation, comprising a source of a substantially planar, sectoral-shaped swath of said radiation arranged on one side of the body part so as to define a plane of interest in the body part, a plurality of detector devices, responsive to said radiation, arranged on the opposite side of said body part to said source and each disposed to receive radiation emergent from the body along a respective path, through said plane of interest, means for rotating the source and the detector devices around the body part and in the plane of the swath at a steady speed and through a predetermined angle, and means for deriving from each of said detector devices during said rotation a plurality of distinguishable signals indicative of the absorption suffered by said radiation on traversing a respective group of paths through said body part.

Figure 2:
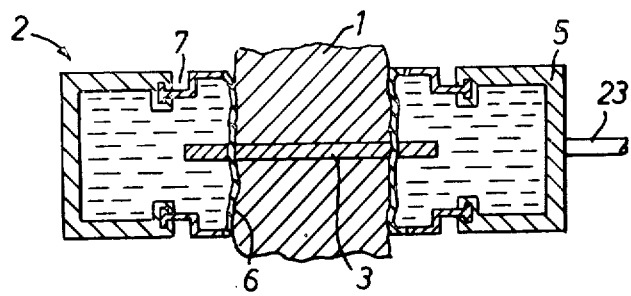
Figure 4A:
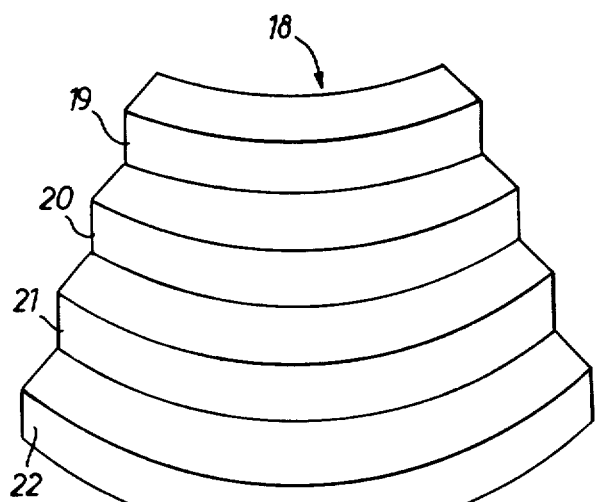
Figure 3:
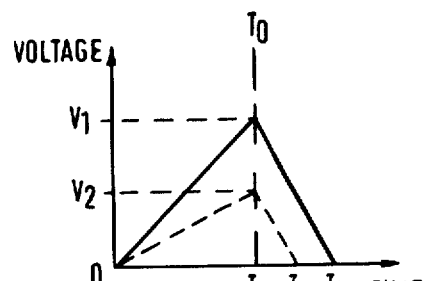
Figure 5:
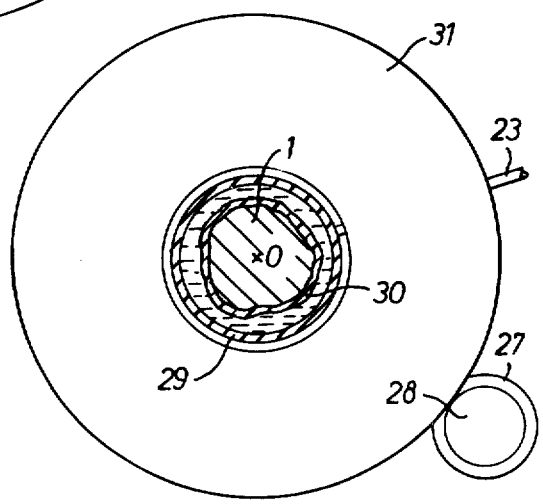
Figure 4B:
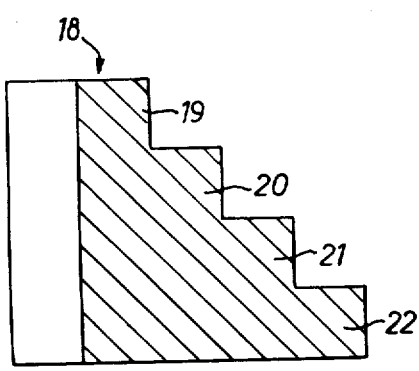

In order that the invention may be clearly understood and readily carried into effect, the same will now be described, by way of example only, with reference to the accompanying drawings, of which:

FIG. 1 illustrates, partly in a plan section and partly in block schematic form, apparatus in accordance with one example of the invention, FIG. 2 shows a section on lines II—II of FIG. 1, FIG. 3 illustrates waveforms explanatory of the operation of the apparatus show in FIG. 1, FIGS. 4a and 4b show, in perspective view and cross-sectional form respectively, a calibration device suitable for use with the apparatus shown in FIG. 1, and FIG. 5 shows an alternative form of the invention.

Referring now to the drawings, and more particularly to FIGS. 1 and 2, a body 1 to be investigated is mounted in an arrangement shown generally at 2 so that it can be illuminated by a fan-shaped swath 3 of penetrative radiation, such as X- or γ-radiation, derived from a source 4.

The arrangement 2, in this example, comprises an enclosure of which the outer walls 5 are formed of the material known by the Registered Trade Mark "Perspex" or another suitable material. The arrangement is provided with a central aperture in which the body 1 is situated, the aperture being surrounded by a tubular, flexible wall 6 formed, for example, of rubber. The enclosure between the walls 5, 6 is filled with water as indicated by the horizontal shading lines. Water can be pumped into or out of said enclosure by means of a pump 24 which is reversible in its operation and which communicates with said enclosure by means of a pipe 23 and with a water reservoir (not shown) via a pipe 25, a closure valve 25a and a removeable pipe 25b. Water is pumped out of said enclosure to allow the tubular wall 6 to expand outwardly so that the body 1 can be inserted therein and then water is pumped into said enclosure to cause the wall 6 to fit snugly around the part of body 1 which is to be investigated. In order that the body 1 and the flexible wall 6 may remain stationary whilst the remainder of the enclosure is rotated, a rotary water seal 7 is provided in the arrangement 2. The fan shaped sweep 3 passes through the arrangement 2 as shown in FIG. 2 and it will be appreciated that the snug fit between the flexible wall 6 and the body 1 must be maintained at least over the area through which the beam passes.

Having passed through the body 1, the fan shaped sweep 3 is incident upon a plurality of radially extending collimators 8 and the field of view of each collimator defines a respective, discrete path of radiation through the body 1. In one example, 160 such collimators are used. In order that the overall degree of absorption of radiation along each discrete path can be monitored, each collimator 8 communicates with a respective radiation detector 9 which may take one of several forms to be described hereinafter.

Each detector 9 feeds a respective integrator circuit 10 and the arrangement is such that (referring to FIG. 3) each integrator receives signals from its respective radiation detector for a given exposure period $T_o$. At time $T_o$, a negative voltage is applied in parallel to all the integrators 10 causing them each to discharge towards zero potential. The time taken for the charge held in a give integrator to reach zero potential will clearly be determined by the amount of charge accumulated up to $T_o$, thus if, for example a first detector accumulated charge corresponding to a potential $V_1$ and a second detector accumulated a lesser amount of charge corresponding to a potential $V_2$, the integrator associated with the first detector would reach zero potential in time $(T_1-T_o)$ whereas the integrator associated with the second detector would reach zero potential in the lesser time $(T_2-T_o)$. Accordingly, referring again to FIG. 1, each integrator 10 is arranged to feed a respective bistable circuit 11 which is such that it provides an output pulse when the input signal thereto reaches zero potential from a more positive potential. The output pulses from all the circuits 11 pass on the one hand through a common OR gate 11a, and on the other hand as path identity signals to a store 12 associated with a computer (not shown).

An oscillator 13 is arranged to generate regularly occurring pulses at a rapid rate and these are applied to an AND gate 14. The gate 14 is enabled at time $T_o$ by the same control signal as was used to apply the negative potential to the integrator 10, the control signal being applied to a terminal 15, and is arranged to pass the pulses generated by oscillator 13 to a counter 16 continuously from the time $T_o$ to the time when the last of the integrators indicates zero potential.

The counter 16 is a multistage binary counter having sufficient capacity for counting the number of pulses which would be generated by oscillator 13 during the period from $T_o$ to the maximum possible time taken for one of the integrators 10 to indicate zero potential i.e., in the case of zero absorption of the radiation along a given path.

Each stage of counter 16 is connected, via a respective AND gate 17, as a decay time input to the store 12 and the gates 17 are all simultaneously enabled when a pulse derived from any one (or more) of the bistable circuits 11 passes through to OR gate 11a. The store 12 thus receives both path identity and decay time information and the computer is arranged to correlate this information to provide a figure representing the absorption (or transmission) of said radiation along each path. These figures are then converted into logarithmic values and processed, for example in the manner described in the aforementioned Patent Specification, to provide a representation or a visual record or display of the absorption (or transmission) coefficients of substantially all the elements in a two-dimensional notional matrix of elements defined in the body 1.

In this example, the fan shaped swath is substantially planar, but it could alternatively be caused to have a greater thickness dimension so as to permit a three dimensional notional matrix of elements defined in the body 1 to be investigated.

In operation, the source 4, the part of arrangement 2 outside the water seal 7, together with the pump 24, pipes 23 and 25 and the valve 25a, from which pipe 25b is then detached, the collimators 8 and the detectors 9 are orbited, about the centre 0 of the arrangement 2, relative to the body 1 in order to expose the body 1 to radiation from a plurality of different directions. For this purpose the aforementioned components are mounted on a turntable 26 which has an aperture therein corresponding to the diameter of the water seal 7, the turntable being driven by means of an electric motor 27 via a suitable drive mechanism 28 which may comprise, for example, a toothed gear wheel adapted to co-operate with gear teeth provided around the periphery of the turntable 16. It is preferable in some circumstances, especially when the human torso is examined, that the aforementioned components be rotated at a rapid rate in order that the irradiation of the torso can be completed sufficiently rapidly that the time available for movement of internal organs of the body (which movement could cause degradation of the resolution of the apparatus) is limited. In these circumstances, it is preferable for the aforementioned components to be rotated continuously rather than step-wise (as described in some embodiments of the apparatus described in the aforementioned Patent Specification). Because of this continuous rotation, each exposure time effectively corresponds to the time taken for the aforementioned components to rotate through a small angle, and in order to reduce or avoid confusion of detail produced by the relative movement between the source and detectors and the body, the computer can be programmed to take account of this.

To evaluate zero for each detector 9 during operation of the apparatus, a shutter (not shown) may be provided between the source 4 and the arrangement 2. This shutter is rotates so that it intermittently interrupts the radiation during each exposrue time and the zero reading obtained when the beam of radiation is interrupted is subtracted from the calculated absorption (or transmission) coefficient. The shutter drive mechanism must be synchornised with the mechanism for rotating the aforementioned components of the apparatus so as to enable a zero to be evaluated during each exposure time.

It is possible, as previously mentioned, to utilise one of several arrangements as the detectors 9 and these arrangements are set out below.

EXAMPLE 1

Silicon photodetectors together with an associated wavelength converter phosphor, such as a CsI crystal, for converting the penetrative radiation into optical radiation. The silicon photodetectors can take the form, for example, of p-n junction photodiodes, p-i-n silicon photodiodes, silicon avalanche photodiodes, silicon photofets, silicon planar junction phototransistors or silicon photo-integrated circuits, a respective detector being provided for each collimator.

A problem which arises with photodetectors of this kind is dark current and the detectors require cooling to reduce this phenomenon. If however, the temperature of the array of detectors is stabilised, a higher dark current can be tolerated since it is consistent and can be allowed for by suitably programming the computer.

EXAMPLE 2

Photoemissive diodes together with a wavelength converter phosphor. The diode could comprise, for example, respective separate photodiodes for each collimator; a similar number of diodes in a common vacuum enclosure; channel multiplier diodes; small photomultipliers or gas-filled photomultiplier photocells.

There are practical limitations on attainable sizes of photoemissive diodes, but this disadvantage can be alleviated to some extent by utilising reflecting optical systems.

EXAMPLE 3

An X-(or $\gamma$-) ray sensitive vidicon. Grazing incidence reflecting optical elements made from such metals as electroless plates titanium or aluminium have made it possible to obtain good quality X-ray images without using pinhole optics. A difficulty arises however in that an image demagnefication of about 30:1 is required.

EXAMPLE 4

A fibre-optic vidicon fed by respective fibre optic light guides from respective wavelength converter phosphors for each collimator.

EXAMPLE 5

A Digicon tube and a wavelength converter phosphor. The Digicon is a vacuum tube containing a semi-transparent photosmissive cathode of the inside of the end window, a series of accelerating and focusing electrodes and a linear array of silicon p-n junction diodes on the window at the other end. A solenoidal focus field is used to direct and focus electrons emitted from the photocathode. The diodes are reverse biassed and, when struck by electrons, the phenomenon of electron bombardment induced conductivity causes them to conduct. The conduction current is about $2 \times 10^4$ or $3 \times 10^3$ times greater than the bombarding current and thus the tube is capable of detecting single photoelectrons. For this application, the Digicon requires a fibre optic end window communicating with the photocathode and fibre optic coupling between the Digicon and respective wavelength converter crystals for each collimator.

EXAMPLE 6

Photographic film. A full size medical X-ray plate is moved mechanically beneath the body in a direction perpendicular to the plane of the fan-shaped beam 3. Thus a series of lines corresponding to the transmitted radiation would be unprinted as a number of dots at each exposure angle. After developing the lines are scanned with a microdensitometer.

In any of the above examples, it can be advantageous, in order to avoid dead spaces between adjacent detectors, to construct the collimators so that adjacent paths overlap to some extent. Alternatively, however, the gaps may be covered by arranging that, in a full 360° sweep around the body, the paths not scanned on one half revolution are scanned during the next half revolution.

It is desirable, in any of the foregoing arrangements, that the individual components of the detecting means should initially be calibrated and then re-calibrated before each new body is examined thereby. To this end, a suitable arrangement has been found to be as follows.

One of the individual components (such as for example the extreme left hand collimator 8 and detector 9 shown in FIG. 1) is calibrated comprehensively by insertion of a wedge of continuously variable thickness (and hence absorbing power) between the source 4 and the collimator 8, and the output signals fed from counter 16 to the computer are noted. Thus the computer is provided with a characteristic response curve for the detecting means. Of course the wedge could be inserted between the source 4 and all the detecting means to enable an average characteristic response curve to be calculated, if desired. Once having provided the computer with a characteristic response curve, it is only necessary, during re-calibration, to provide relatively crude information to the computer, for example an indication of the responses of the detecting means to minimum and maximum amounts of radiation would be sufficient. However in this example the responses of the detecting means under two intermediate conditions, as well as under the two extreme conditions are measure. A sectoral shaped calibration member 18, made up of four layers as shown in FIGS. 4a and 4b is used, the thinnest layer 19 being adapted to transmit substantially all radiation incident thereon, the next thicker layer 20 being adapted to absorb the radiation to some extent, the layer 21 being adapted to absorb the radiation to a greater extent and the thickest layer 22 being adapted to absorb substantially all the radiation incident thereon. In addition to, or instead of being of different thicknesses the layers may be of different materials. In operation, the calibration member 18 is lowered step-wise into the path of the fan-shaped swath 3, so that the amount of radiation passed through each layer of member 18 is monitored by each detecting means and the output signals derived from the detecting means are processed as described with reference to FIG. 1, the process terminating in a rough re-calibration curve for each component of the detecting means being applied to the computer for comparison with the stored characteristic response curve. After the comparison has been effected, the computer has a store of calibration error information which can be used automatically to weight the signals derived from respective detecting means.

The "Perspex" wall 5 of the arrangement 2 need not be of the shape shown in FIG. 1. For example the walls through which the beam 3 passes need not be arcuate; they may be planar or shaped to provide a constant attenuation to radiation throughout the arrangement 2 when the body 1 is replaced by water. Moreover, the material used to construct these walls need not be "Perspex" for example PVC or other suitable plastics materials could be used.

In the apparatus described with reference to FIG. 1, the discharge rate of the integrators 10 is arranged to be linear, and for this reason the binary numbers fed into the store 12 from the counter 16 have to be converted into logarithmic values in order that the overall absorption suffered by radiation traversing the body along a path can be expressed as the sum of the absorptions of the elements of the matrix which are disposed along said path.

An alternative arrangement is to cause the integrators to discharge in accordance with a logarithmic law. When the charge held in an integrator has decayed to a threshold level, the corresponding bistable circuit 11 is arranged to feed a pulse via "OR" gate 11a to the 'AND' gates 17. The operation from this point is the same as that described with reference to FIG. 1 except, of course, that the logarithmic conversion has already taken place so that it is unecessary for the members fed into store 12 from the counter 16 to be so converted.

The threshold level referred to in the last preceding paragraph can be selected to suit individual applications and if a human torso is being examined, the threshold may be made such that an absorption level giving rise to a charge, in an integrator, which decays to the threshold level in a given time $t'$ is allocated a value of zero. Correspondingly, absorption levels giving rise to changes which decay to the threshold level in times less than $t'$ are designated positive (since greater absorption has occurred) whereas absorption levels giving rise to changes which decay to the threshold level in times greater than $t'$ are designated negative.

It will be appreciated that in practice it is convenient for a patient to lie supine with the required part of his torso inside the tubular, flexible wall 6. This can be achieved by arranging the apparatus with its axis of rotation horizontal and by placing suitable couches or the like on either side of the apparatus, the couches being adapted to support, respectively, the upper part and the lower part of the patient's body.

In a modification of the invention which is shown in part in FIG. 5, the rotary water seal used in the apparatus shown in FIG. 1 is dispensed with since the water enclosure is designed to remain stationary while the source and detectors orbit around it. In the apparatus shown in plan and part cross-sectional view in FIG. 5, a cylindrical outer wall 29 of "Perspex" (Registered Trade Mark) or other suitable material is formed with annular end flanges (not shown). Extending between the inner peripheries of the two annular flanges is a tubular, flexible inner wall 30 formed, for example, of rubber. The X-ray source and detectors (not shown) are mounted on a turntable member 31 which is annular and rotates around the cylindrical wall 29; the axis of rotation of the turntable being coincident with the longitudinal axis of the cylindrical wall 29. The operation of the apparatus is identical to that of FIG. 1 but since the water enclosure does not rotate, the need for the rotating water seal is avoided. Also, it is possible to provide a permanent connection between a water pump such as (FIG. 1) and a water reservoir, avoiding the need for a valve such as 25a and a removeable pipe such as 25b (FIG. 1).

Although in the foregoing description reference has been made to the use of water to surround the part of the body being examined, it is stressed that the invention is not limited to the use of water. Other liquid media may be used and, in particular if the body being examined is not a human body, other liquids of different densities might be preferable to water. In general it is desirable to choose the liquid medium such that its absorption to the radiation being used is similar to the average absorption of said radiation by the body being examined.

What we claim is:

1. Medical diagnostic apparatus for examining a slice of the body of a patient to produce a representation of the variation of an X-radiation response characteristic of said slice, the apparatus comprising:
   a source of X-radiation for generating a fan-shaped swath of radiation;
   a support on which said source is supported;
   a futher support to position the patient so that said swath of radiation will be propagated through said slice of the body;
   a plurality of detectors for receiving radiation after propagation through said slice, said detectors being arranged with respect to each other to receive radiation along narrow beam paths angularly displaced across substantially the whole of said fan-shaped swath of radiation and said detectors being disposed so that radiation propagated through the slice along any two adjacent beam paths is received by different detectors;
   means for rotating at least said source continuously through a substantial angle about an axis intersecting said slice to cause said swath to assume successive different angular positions relative to the body;
   means for sensing radiation received by said detectors during successive increments of said continuous rotation of said source, said means generating respective electrical output signals relating to the radiation propagated to the detectors along said narrow beam paths angularly displaced across said swath during said successive increments of continuous rotation; and
   means responsive to said electrical output signals for producing said representation of the variation of an X-radiation response characteristic of said slice.

2. Apparatus according to claim 1, said sensing means including:
   means for generating an analog signal representing the radiation received by each of said detectors during each of said successive increments of continuous rotation of said source; and
   means for converting said analog signal to a digital signal, said converting means being common to at least a plurality of said detectors.

3. Apparatus according to claim 1 in which said plurality of detectors are supported by said first mentioned support so as to rotate with said source, said detectors receiving radiation through said body along respective ones of said narrow beam paths angularly displaced across the fan.

4. A medical radiology device comprising:
   means for defining a patient position;
   means disposed outside the patient position for generating X-radiation propagating in a substantially planar region defining a slice of the patient position and emerging therefrom after suffering absorption determined by the matter along its path through said slice;
   means for orbiting the generating means around the patient position in the plane of said slice;
   means for detecting the radiation emerging from said slice and including a plurality of indicating means each indicating the radiation emerging from the slice along one of a plurality of beam paths which traverse the patient position along said slice, said beam paths having finite widths in the plane of the slice, any spacing between adjacent beam paths in the plane of the slice being by a distance substantially less than the width of a beam path, each indicating means successively indicating the radiation emerging from the slice after traversing the slice at successive angular positions of the generating means with respect to the patient position;
   means for providing measurement signals determined by the radiation indicated for said beam paths by the indicating means; and
   means for combining said measurement signals to form a representation of the distribution of the X-radiation absorption or transmission characteristics of the matter within said slice, said representation selectivity including a representation of soft tissue of a patient at the patient position.

5. A medical radiology device as in claim 4 including means for orbiting the detecting means around the patient synchronously with the orbiting of the generating means.

6. A medical radiology device as in claim 4 wherein the detecting means include means for generating an analog signal indicating said radiation detected along each beam path and means for converting the analog signals to a digital signal, said converting means comprising major components capable of being concurrently used to convert to digital signals a plurality of said analog signals.

7. Apparatus for examining a slice of a body by means of penetrating radiation, such as X-radiation, including a radiation source, disposed to one side of said body and arranged to project a flat, fan-shaped swath of said radiation through said slice of the body, a plurality of detector devices, responsive to said radiation, disposed at the other slice of said body to said source, and each disposed to receive radiation emergent from said slice along a respective one of a set of beam paths disposed at a first mean angle in said slice, the paths of said set diverging in travelling from said source to said detector devices and the detector devices extending over substantially the whole of said swath and having radiation receiving surfaces dimensioned to substantially conform to the cross-sectional dimensions of said paths; neighbouring detector devices being closely adjacent so that radiation projected through said slice along any two adjacent beam paths in said set is received by different detector devices, a support member supporting said source and said detector devices, means for angularly moving the support member, and with it said source and said detector devices, around the body about an axis intersecting said slice to cause said radiation to be projected through said slice along further sets of beam paths at different mean angles in said slice, and means for deriving from each detector device, during said angular movement, a sequence of electrical signals, each signal being indicative of the absorption suffered by said radiation on traversing a beam path in a respective one of said sets.

8. Apparatus according to claim 7 wherein said means for deriving signals from said detector devices comprises, for each device, an integrator circuit and a bistable circuit, there being also provided first circuit means for causing each of said integrators to accumulate, over a given period, a charge indicative of the amount of said radiation incident on the respective detector device during that period, and means operative after the expiry of said period to cause the charges held in the integrators to discharge towards a reference level, the bistable circuit in each case being arranged to produce an output pulse when the discharge has been effected, and second circuit means, including a counter circuit, for responding to the output pulses from said bistable circuits to produce information indicative of the duration of each discharge and of the path to which it relates.

* * * * *